(12) United States Patent
Wallace et al.

(10) Patent No.: US 10,391,291 B2
(45) Date of Patent: Aug. 27, 2019

(54) IMPLANT INSERTION SYSTEM

(71) Applicants: Robert F. Wallace, Fort Myers, FL (US); Matthew Q. Shaw, Carmel, IN (US)

(72) Inventors: Robert F. Wallace, Fort Myers, FL (US); Matthew Q. Shaw, Carmel, IN (US)

( * ) Notice: Subject to any disclaimer, the term of this patent is extended or adjusted under 35 U.S.C. 154(b) by 1093 days.

(21) Appl. No.: 13/633,268

(22) Filed: Oct. 2, 2012

(65) Prior Publication Data

US 2014/0094767 A1  Apr. 3, 2014

(51) Int. Cl.
*A61M 37/00* (2006.01)

(52) U.S. Cl.
CPC ................ *A61M 37/0069* (2013.01)

(58) Field of Classification Search
CPC ............ A61M 5/178; A61M 2025/024; A61M 2025/02; A61M 39/14; A61M 37/0069; A61B 17/34
See application file for complete search history.

(56) References Cited

U.S. PATENT DOCUMENTS

| | | | | |
|---|---|---|---|---|
| 3,685,795 | A * | 8/1972 | Caster | F16K 13/04 251/335.3 |
| 4,518,383 | A * | 5/1985 | Evans | A61B 17/3401 604/170.03 |
| 5,250,026 | A | 10/1993 | Ehrlich et al. | |
| 5,284,479 | A * | 2/1994 | de Jong | A61M 37/0069 604/130 |
| 6,120,786 | A * | 9/2000 | Cherif Cheikh | A61M 37/0069 424/423 |
| 6,648,849 | B2 * | 11/2003 | Tenhuisen | A61M 37/0069 424/423 |
| 6,896,670 | B2 * | 5/2005 | Cherif Cheikh | A61M 5/3257 604/506 |
| 7,214,206 | B2 | 5/2007 | Rue et al. | |
| 7,780,625 | B2 | 8/2010 | Bardy | |
| 7,914,512 | B2 | 3/2011 | Orth et al. | |
| 8,029,458 | B2 | 10/2011 | Cherif-Cheikh et al. | |
| 2004/0147882 | A1 * | 7/2004 | Kunitomi | A61M 25/0637 604/263 |

(Continued)

FOREIGN PATENT DOCUMENTS

| | | |
|---|---|---|
| FR | 2277568 | 2/1976 |
| WO | WO9830274 | 7/1998 |

OTHER PUBLICATIONS

Merriam-Webster Dictionary. Accessed online Sep. 30, 2016. Removable. Definition (1)(a) and (2).*

(Continued)

*Primary Examiner* — Bhisma Mehta
*Assistant Examiner* — Matthew A Engel
(74) *Attorney, Agent, or Firm* — Rathe Lindenbaum LLP (57) ABSTRACT

A needle shell is inserted through skin with a needle insert within the needle shell occluding an insertion end of the needle shell. The needle insert is withdrawn from the needle shell and an implant tube is inserted into the needle shell and below the skin, wherein the implant tube is slid within the needle shell while the needle shell is below the surface of the tissue. Interior surfaces of the implant tube contact and guide sliding movement of the implant. An implant insertion rod is inserted into the needle shell to implant an implant below the skin.

8 Claims, 8 Drawing Sheets

(56) References Cited

U.S. PATENT DOCUMENTS

| | | | |
|---|---|---|---|
| 2006/0094983 A1 | 5/2006 | Burbank et al. | |
| 2007/0038145 A1* | 2/2007 | Field | A61B 90/17 600/562 |
| 2008/0071246 A1 | 3/2008 | Nazzaro et al. | |
| 2008/0249466 A1* | 10/2008 | Aubert | A61M 31/007 604/117 |
| 2008/0300546 A1 | 12/2008 | Godara et al. | |
| 2009/0209903 A1* | 8/2009 | Cherif-Cheikh | A61M 37/0069 604/63 |
| 2009/0216181 A1 | 8/2009 | Speeg et al. | |
| 2010/0125240 A1 | 5/2010 | Spedden et al. | |

OTHER PUBLICATIONS

PCT International Search Report for PCT/US2013/063121 dated Jan. 3, 2014.

\* cited by examiner

IMPLANT INSERTION SYSTEM

BACKGROUND

Therapeutics, vaccines, medicines and drugs (collectively referred to as therapeutics) are sometimes delivered via implants. Existing systems for depositing such implant below the skin are often complex and expensive. Use of such systems may also be complicated, tedious and time-consuming.

BRIEF DESCRIPTION OF THE DRAWINGS

FIGS. 19-24 are side views of another example implementation of the implant insertion system of FIG. 1.

DETAILED DESCRIPTION OF THE EXAMPLE EMBODIMENTS

Figure 1:
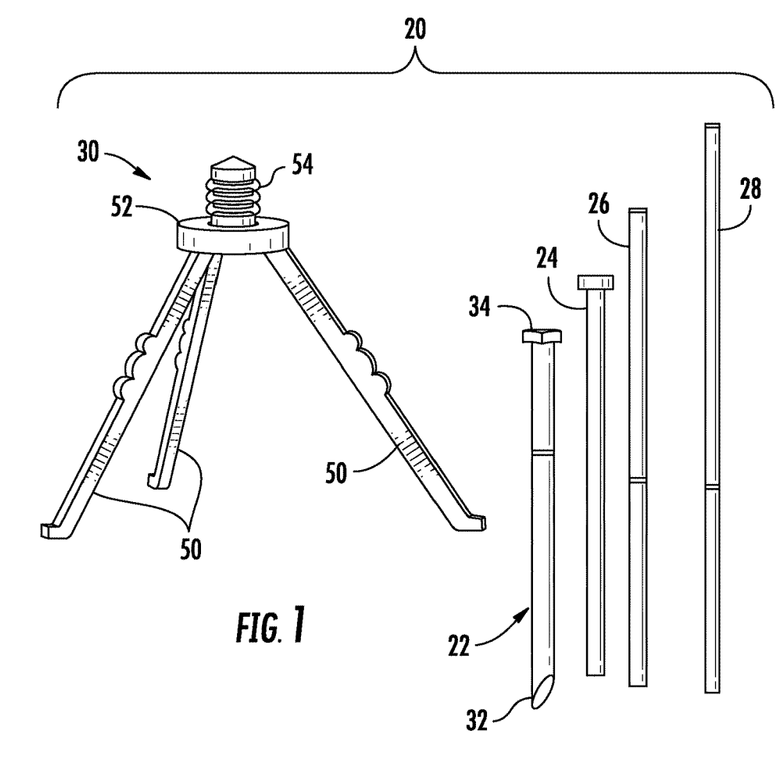
FIG. 1 is a perspective view of an example implant insertion system.
Figure 2:
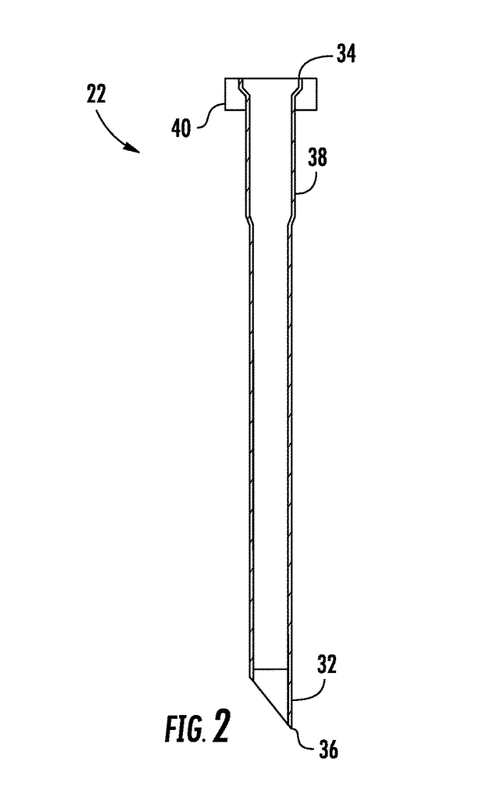
FIG. 2 is a sectional view of an example needle shell of the system of FIG. 1.

FIG. 1 illustrates an implant insertion system 20 for insertion of an implant, such as a solid therapeutic implant, into precise locations of an animal or human body to treat areas of disease, pain or other medical conditions. Insertion system 20 comprises needle shell 22, needle insert 24, implant tube 26, insertion rod 28 and fixture 30. FIG. 2 is a sectional view of needle shell 22.

Needle shell 22 comprises a needle having an insertion end 32 and an opposite loading end 34. In the example illustrated, needle shell 22 has a pointed tip 36 at insertion end 32 (the distal or axial end) for penetrating tissue while loading end 34 (the proximal end) as a serial enlargement 38 to facilitate loading of needle insert 24, implants eg 229, or implant tube 26. In one implementation, needle shell 22 is formed from a stainless steel, titanium alloy or other compatible material. In one implementation, needle shell 22 HAS A TYPICAL, BUT NOT LIMITED TO, a gauge of between 27 gauge and 14 gauge with a wall thickness typically, but not limited to, less than or equal to about 0.15 mm. In one implementation, the enlarged funnel shaped and 38 has an inner diameter of at least about 0.2 mm and a TYPICAL, but not limited to, length of 30 mm whereas needle shell 22 has a typical, but not limited to, length of 100 to 200 mm from portion 38 to tip 36. In one implementation, needle shell 22 may comprise a Tuohy epidural needle or a spinal needle. In other implementations, needle shell 22 may comprise other needle configurations.

In the example illustrated, needle shell 22 additional includes a removable syringe holder or syringe clip 40 removably mounted to loading end 34. Syringe clip 40 facilitates handling needle shell 22 or the injection of liquid through needle shell 22. In other implementations, syringe clip 40 may be integrally formed as a single unitary body with needle shell 22 or may be omitted. In other implementations, needle shell 22 may be formed from other materials and may have other dimensions.

Needle insert 24 comprises an elongate member configured to fit within and through interior lumen of needle shell 22. Needle insert 24 facilitates placement of needle shell 22 through tissue by helping to maintain the shape of needle shell 22 during such insertion. In one implementation, needle insert 24 further includes a blocked or closed end, allowing insert 24 to occlude or block insertion end 32, inhibiting entry of tissue or fluids into needle shell 22.

Figure 3:
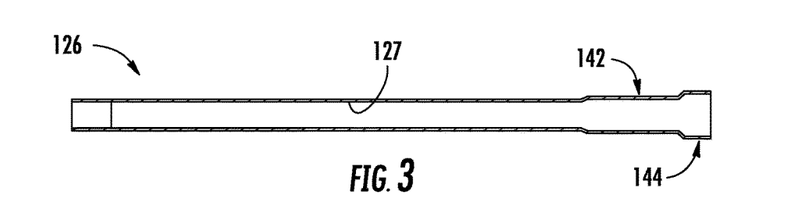
FIG. 3 is a sectional view of an example implant tube of the system of FIG. 1.

Implant tube 26 comprises an elongate tube or roll insertable through needle shell 22 and configured to carry an implant, such as a solid therapeutic implant. FIG. 3 is a sectional view illustrating implant tube 126, one example of implant tube 26. As shown by FIG. 3, implant tube 126 comprises an elongate tube which is reloadable with implants and which has interior surfaces 127 which are to contact and guide sliding movement of an implant that is to be contained within tube 126. To facilitate loading, implant tube has an enlarged funnel shaped mouth 142 at a loading and 144. In the example illustrated, implant tube 126 has a wall thickness of less than or equal to 0.1 mm, facilitating loading of larger implants. Implant tube 126 has an outer diameter sized such that implant tube 126 may slide into and out of needle shell 22 smoothly. In one implementation, implant tube 126 may additionally include depth markers or other depth identifying indicia proximate to loading end 144, providing a caretaker within indication of a gap in which tube 126 has been inserted. In addition to locating an implant within and through needle shell 22, implant tube 26 further provides the caretaker or the option of injecting liquid medicines at any time during a procedure by attaching a syringe to the top of the implant tube.

Figure 4:
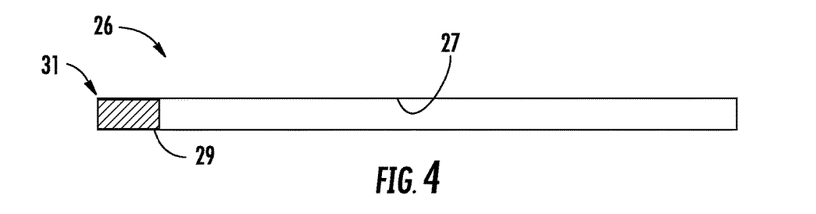
FIG. 4 is a sectional view of another example implant tube of the system of FIG. 1.

FIG. 4 illustrates implant tube 26 in more detail. Implant tube 26 is similar to implant tube 126 except that implant tube 26 is prepackaged with one or more implants 29. In one implementation, implant 29 is removably retained within tube 26 by friction. In another implementation, implant 29 is removably retained within tube 26 by a temporary adhesive or by a severable or breakable tether. In one implementation, implant 29 is retained within tube 26 by a breakable end flap or film across the insertion end 31 of tube 26. As will be described hereafter, during withdrawal of implant 29 from tube 26, the implant 29 and tube 26 slide relative to one another, the implant 29 sliding relative to interior surfaces 27 which contact and guide such sliding movement of implant 29. Although tube 26 is illustrated as containing a single implant 26, in other implementations, tube 26 may contain a series of implants 26, wherein each implant 29 may be identical or wherein each implant 29 may contain different implanting materials such as different medicines or therapeutics. In such an implementation, tube 26 facilitates the implanting of multiple implants at different locations within an anatomy without having to reinsert a new implant tube and without having to reload an implant tube. In one implementation, prepackaged implant tube 26 may additionally include a largemouth similar to mouth 142 of tube 126, facilitating subsequent loading of new implants within tube 26 once the prepackaged implant 29 has been implanted. As with tube 126, in some implementations, tube 26 may additionally include one or more depth indicators or indicia.

Insertion rod 28 comprises a semi-rigid rod or plunger configured to smoothly slide into and out of implant tube 26 or 126. Insertion rod 28 is configured to contact and bear against an implant within implant tube 26, 126 as the implant tube 26, 126 and needle shell 22 are moved relative to the implant and rod 28 to withdraw tube 26, 126 and needle shell 22 and to deposit the implant. In one implementation, insertion rod 28 may include depth indicating marks or indicia along its length which indicate a gap that which the implant is being deposited.

Fixture 30 comprise a mechanism for holding or securing insertion rod 28 in place as needle shell 22 is moved and withdrawn relative to insertion rod 28 and the positioned implant. In the example illustrated, fixture 30 comprises a multi-legged pod, such as a tripod. Fixture 30 comprises three extendable legs 50, and a body holder 52 including an insertion rod holder or fastener 54. Body holder 52 includes an internal passage through which insertion rod 28 may pass and slide through. Fastener 54 comprises a tightening device, such as a drill bit tip screw or clip to secure insertion rod 28. In some implementations, system 20 may omit fixture 30 or may include alternate configurations of fixture 30.

Figure 1A:
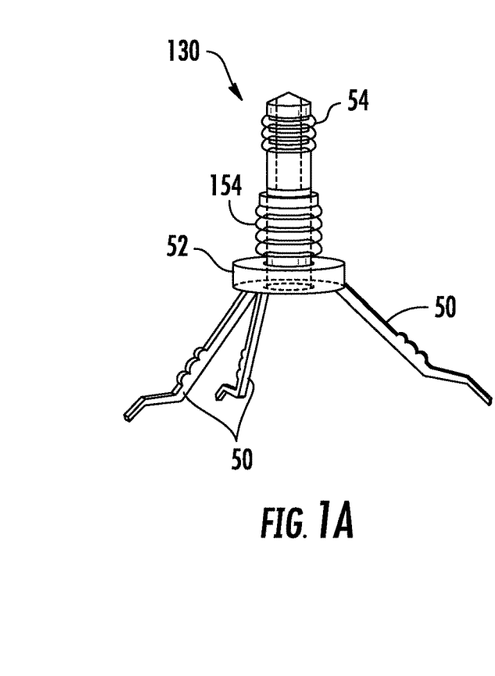
FIG. 1A is a perspective view of an example fixture of the implant insertion system of FIG. 1.

As shown by FIG. 1A, in some implementations, system 20 may additionally comprise a two-stage fixture 130 instead of fixture 30. Fixture 130 is similar to fixture 30 except that fixture 130 additionally includes an implant tube holder 154. Implant tube holder 154 comprises a fastener configured to grip and retain implant tube 26 while implant tube 26 is inserted below the skin 60 (shown in FIG. 8). In one implementation, implant tube holder 154 comprises a tightening mechanism which frictionally bears against a side of implant tube 26. Examples of such a tightening mechanism include, but are not limited to, a drill bit tip screw or a clip which fix a position of the implant tube 26. Implant tube holder 154 retains implant tube 26 in place as implants are loaded through implant tube 26 and/or as insertion rod 28 positions the loaded implants. Implant tube holder 154 can also hold implant tube 26 in fixed position to allow the sliding back of needle shell 22.

Figure 5:
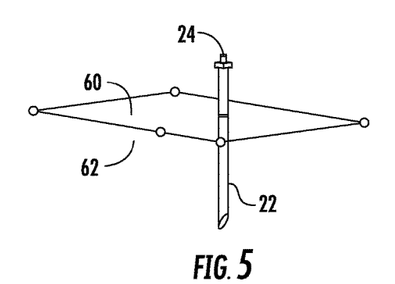
FIG. 5 is a perspective view illustrating positioning of a needle shell and needle insert of the system of FIG. 1 through skin.

FIGS. 5-8 illustrate an example method for implanting an implant that may be carried out using system 20. As shown by FIG. 5, needle shell 22 with an inserted needle insert 24 is inserted through the skin 60 and into the body 62 of an animal or person to receive an implant. In one implementation, the needle shell 22 and/or the needle insert 24 includes a radiopaque marker at an insertion end to facilitate use of x-ray or sonic imaging to precisely locate the insertion end 32 of needle shell 22 into the spine, internal bone, organs or other parts of the body.

Figure 6:
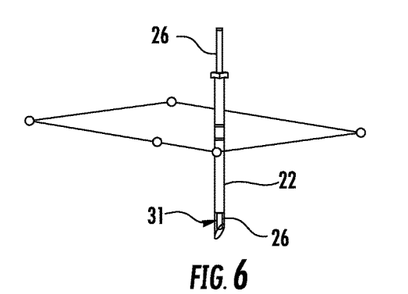
FIG. 6 is a perspective view illustrating positioning of an implant tube through the needle shell of FIG. 5.

As shown by FIG. 6, once the needle shell 22 has been placed, needle insert 24 is removed from needle shell 22 and implant tube 26 is inserted through needle shell 22. Implant tube 26 is passed through needle shell 22 until the end of implant tube 26, 126, 226 located at insertion end 32. In one implementation, implant tube 26 may comprise implant tube 126, wherein the implant is subsequently loaded into tube 126. In another implementation, implant tube 26 may comprise implant tube 226, wherein the implant is prepackaged within implant tube 226. Because implant tube 26 (comprising either tube 126 or tube 226) is inserted after needle shell 22 has already been inserted, the likelihood of the implant within tube 26 becoming contaminated with body fluids or body tissue is reduced.

Figure 7:
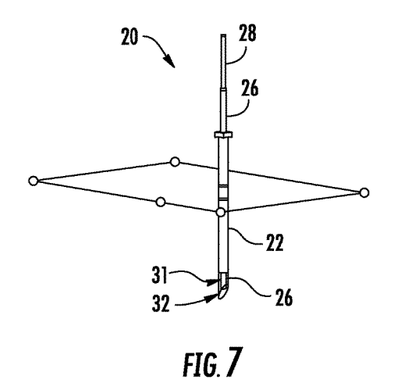
FIG. 7 is a perspective view illustrating positioning of an insertion rod through the implant tube of FIG. 6.
Figure 8:
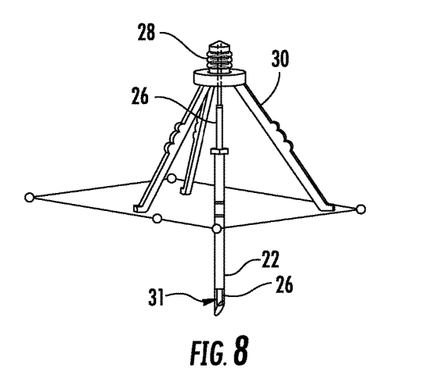
FIG. 8 is a perspective view of an example fixture retaining the insertion rod of FIG. 7.

As shown by FIG. 7, insertion rod 28 is inserted into implant tube 26. In one implementation, insertion rod 28 presses or pushes the implant towards and to insertion end 32 of needle shell 22. In one implementation, insertion rod 28 includes graduation marks for indicating a depth at which the implant is located. Insertion rod 28 holds and maintains the implant (such as implant 29 shown in FIG. 4) in place as implant tube 26 and possibly shell 22 are withdrawn relative to insertion rod 28. As shown by FIG. 8, in one implementation, fixture 30 may be positioned against skin 60 while receiving insertion rod 28. Fastener 54 may be actuated to grip insertion rod 28. By fixing a top of insertion rod 28 in relationship to skin 60, the relative position of the implant is also a fixed. Thereafter, the needle shell 22 and implant tube 26 are slid along the axis of insertion rod 28. Fixture 30 facilitates precise positioning of the implant. In other circumstances where placement of the implant need not be as precise, such as insertion into fatty tissue, use of fixture 30 may be omitted.

Figure 9:
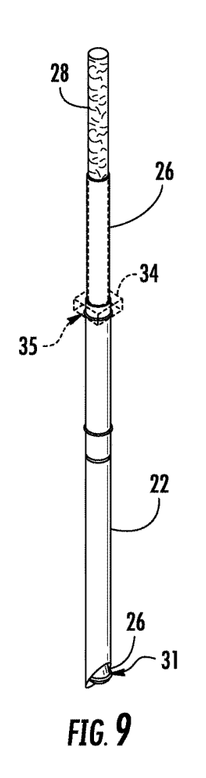
FIG. 9 is a perspective view illustrating the implant tube locating an implant.
Figure 10:
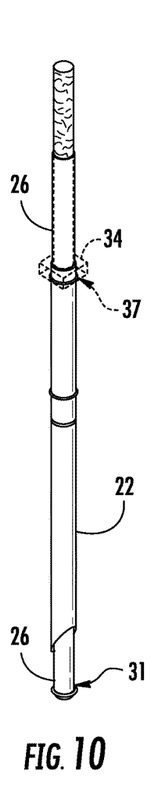
FIG. 10 is a perspective view illustrating withdrawal of the needle shell relative to the implant tube.
Figure 11:
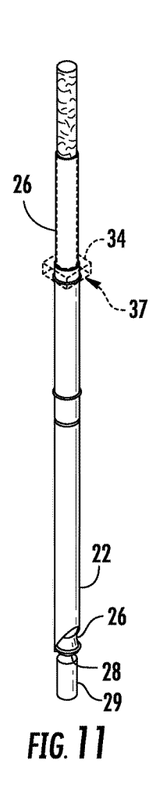
FIG. 11 is a perspective view illustrating withdrawal of the implant tube relative to the insertion rod.
Figure 12:
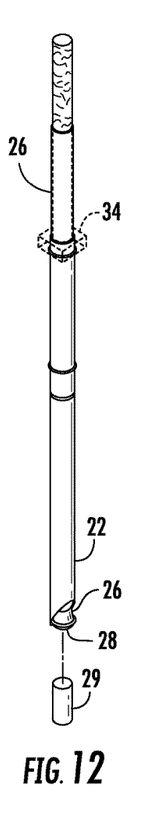
FIG. 12 is a perspective view illustrating further withdrawal of the insertion rod, the implant tube and the needle shell to leave the implant in place.

FIGS. 9-12 illustrate the stepwise withdrawal of needle shell 22 and implant tube 26 to leave the implant in place, the implant being held by recoiled tissue. For ease of illustration, fixture 30 is omitted in FIGS. 9-12. As shown by FIGS. 9 and 10, needle shell 22 is slid along implant tube 26 to withdraw the shell 22 back a length of implant 29 moving end portion 34 from position 35 (shown in FIG. 9) to position 37 (shown in FIG. 10). As shown by FIGS. 11 and 12, the implant tube 26 is then withdrawn back alone, or together with the needle 22, while the implant insertion rod 28 is held steady at the fixed position. Finally, as shown by FIG. 12, needle shell 22, implant tube 26 and insertion rod 28 may all be withdrawn.

In one implementation, insertion rod 28 may push the implant out of implant tube 26. In such an implementation, withdrawal of needle shell 22 results in placement of the implant (being held by recoil tissue). In some implementations, implant tube 26 is left in place after withdrawal of needle shell 22 for use in subsequently delivering medicinal fluids.

Figure 13:
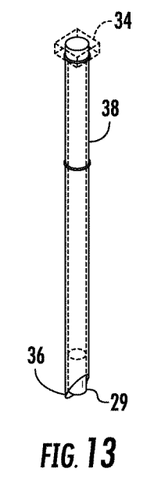
FIG. 13 is a perspective view illustrating loading of an implant directly into and inserted needle shell.
Figure 14:
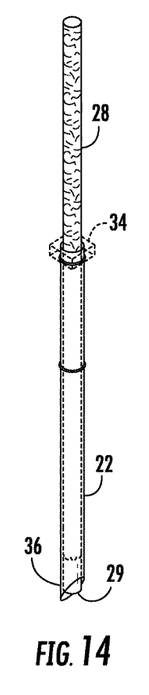
FIG. 14 is a perspective view illustrating loading of an insertion rod into the needle shell to position the implant at an end of the needle shell.
Figure 15:
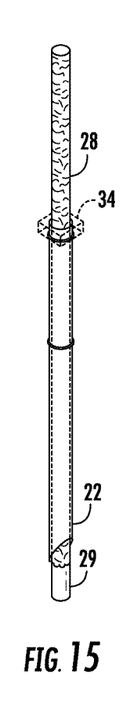
FIG. 15 is a perspective view illustrating withdrawal of the needle shell relative to the insertion rod.

FIGS. 13-16 illustrate another example method for implanting an implant that may be carried out using system 20. In contrast to the method illustrated with respect to FIGS. 5-12, the method shown in FIGS. 13-16 does not utilize implant tube 26. As shown by FIG. 13, after the needle shell 22 has been placed and needle insert 24 has been removed, an implant 29 (or multiple implants 29) yet other may be directly loaded through proximal end 34 of needle shell 22. FIG. 15 illustrates that with a further pushing from implant insertion rod 28, the implant 29 can be positioned at the end 36 of needle shell 22. This can be confirmed by the calculation of depth, as well as feeling the tissue resistance from the insertion rod 28.

Figure 16:
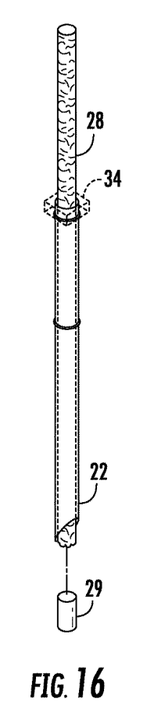
FIG. 16 is a perspective view illustrating withdrawal of the needle shell and the insertion rod to leave the implant in place.

As shown by FIGS. 14 and 15, with the insertion rod 28 holding steady a by fixture (like fixture 30 or a caretaker), the needle shell 22 may be slide back against the insertion rod 28 a depth of the implant 29 (or implants 29), leaving the implant 29 or implants 29 in place and held by recoiled tissue. As shown by FIG. 16, while the implant(s) 29 are held by the recoiled tissue, the fixture can be dissembled stepwise (in the reversed manner as described above), or removed en bloc.

Figure 17:
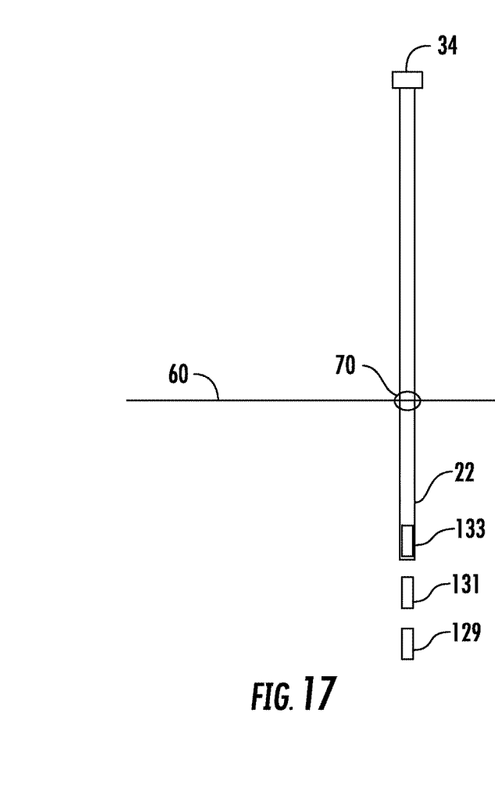
FIG. 17 is a side view of the system of FIG. 1 serially implanting a plurality of implants below the skin.

FIG. 17 illustrates the use of system 20 for the serial placement of multiple implants at different depths using a single entry point 70. To achieve the implantation of multiple implants at different depths, the steps illustrated in FIGS. 5-8 are carried out to position a first implant 129. After such positioning, needle shell 22 is not completely withdrawn from skin 60 but is only partially withdrawn to a shallower depth below skin 60. Thereafter, implant tube 26 is reloaded with a second implant 131 or the existing implant tube 26 is withdrawn from needle shell 22 and a new implant tube 26 with a prepackaged second implant 131 (similar to implant tube 226) is inserted into needle shell 22. Insertion rod 28 is once again inserted through the implant tube 26 to position and hold the second implant 131 in place as needle shell 22 and implant tube 26 are withdrawn, leaving the second implant 131 in place, held by recoil tissue. If a third implant 133 is to be deposited, needle shell 22 is only partially withdrawn to yet shallower depth below skin 60 and the process is repeated to position the third implant 133. The above described method facilitates the implantation of multiple implants at different depths using a single entry point 70. As a result, a caretaker or physician need not completely withdraw and completely reinsert needle shell 22.

Figure 18:
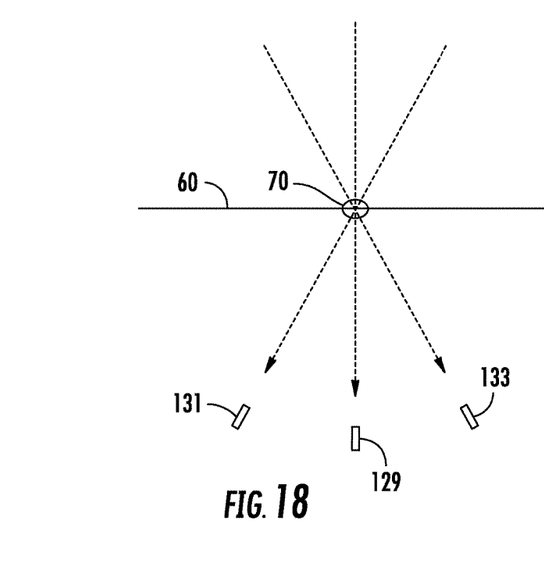
FIG. 18 is a side view of the system of FIG. 1 implanting a plurality of implants below the skin in parallel positions.

FIG. 18 illustrates the use of system 20 for the parallel placement of multiple implants using a single entry point 70. To achieve the parallel implantation of multiple implants, the steps illustrated in FIGS. 5-8 are carried out to position a first implant 129. After such positioning, needle shell 22 is not completely withdrawn from skin 60 but is only partially withdrawn to a shallower depth below skin 60. After removal of implant tube 26, needle insert 24 is reinserted into needle shell 22 to occlude the insertion end of needle shell 22. Thereafter, the shell 22 is reoriented at a different insertion angle and once again pressed to a deeper location, parallel to the first location of the first implant 129. Once insertion end 32 of needle shell 22 is positioned at a desired location (as determined by use of radiopaque marker proximate to insertion end 32 of needle shell 22 or needle insert 24 in some implementations), needle insert 24 is removed and implant tube 26 is passed through needle shell 22. If implant tube 26 comprises implant tube 126 described above, the second implant 131 is loaded. If implant tube 26 comprises implant tube 226 described above, no loading is required as the second implant 131 is prepackaged as part of the implant tube 226. Insertion rod 28 is then inserted through implant tube 26 to locate the second implant 131 at the insertion end 32 of needle shell 22. Thereafter, implant tube 26 and needle shell 22 are slid along insertion rod 28, relative to insertion rod 28, to implant the second implant 131 which is retained by recoiling tissue. To position yet a third implant 133 at a third parallel position, the same process as used for depositing implant 131 may be repeated. The process described with respect to FIG. 18 may be combined with the process described above with respect to FIG. 17 to serially deposit multiple implants at different depths and in parallel positions.

FIGS. 19-24 illustrate implant insertion system 320, another implementation of implant insertion system 20. Implant insertion system 320 is similar to insertion system 20 except that implant insertion system 320 utilizes fixture 330 in place of fixture 30. Those remaining components of insertion system 320 are numbered similarly.

Figure 19:
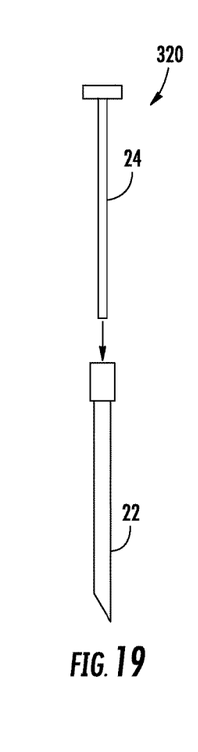
FIG. 19 illustrates insertion of a needle insert into a needle shell.
Figure 20:
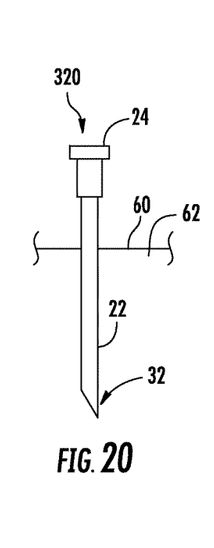
FIG. 20 illustrates positioning of the needle insert a needle shell of FIG. 11 below skin.
Figure 21:
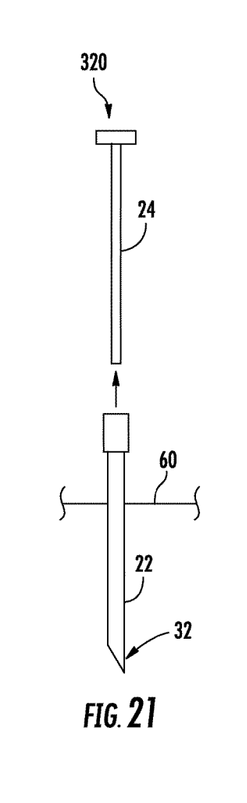
FIG. 21 illustrate withdrawal of the needle insert from the needle shell.
Figure 22:
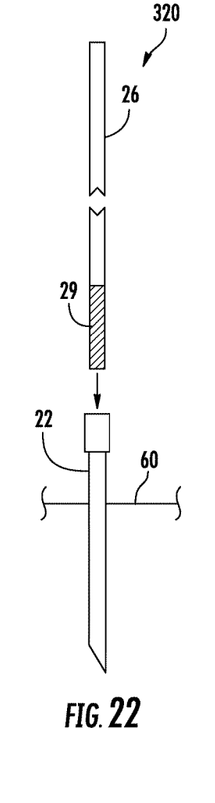
FIG. 22 illustrates insertion of an implant tube into the needle shell.
Figure 23:
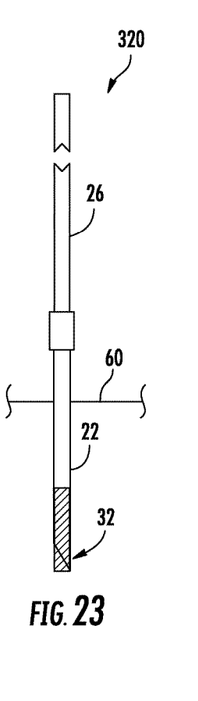
FIG. 23 illustrates complete insertion of the implant tube into the needle shell to position an implant.

As shown by FIG. 19, needle insert rod 24 (illustrated as a disposable rod in the example shown) is inserted into needle shell 22. As shown by FIG. 20, with needle insert rod 24 within needle shell 22, and occluding an insertion end 32 of needle shell 22, is shell 22 is inserted through skin 60 into 62 such a locate insertion end 32 at a desired depth. As shown by FIG. 21, needle insert rod 24 is then withdrawn while leaving needle shell 22 in place. As shown by FIG. 22, implant tube 226 (with the prepackaged implant 29) is inserted into needle shell 22. As shown by FIG. 23, implant tube 226 is inserted so as to position implant 29 proxy to insertion end 32 of needle 22. An insertion rod 28 is then positioned inside the implant tube 226, abutting the upper end of the implant 29.

Figure 24:
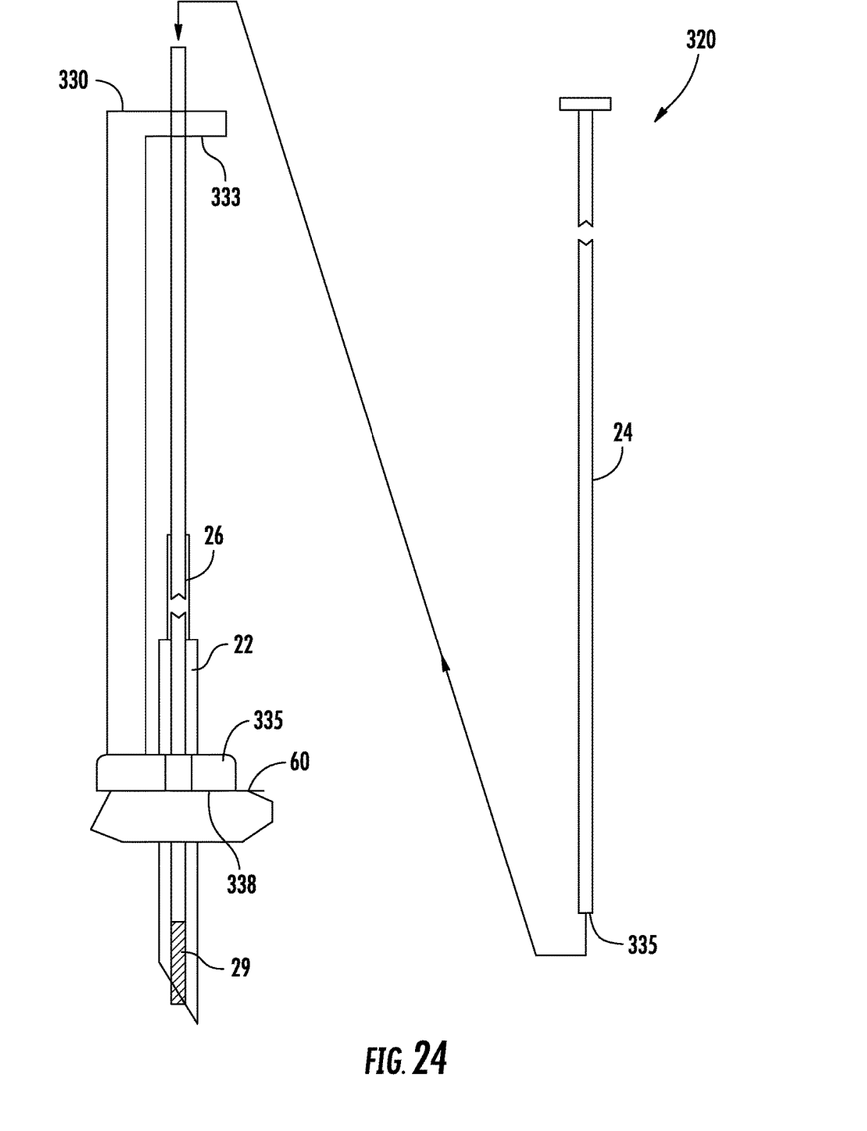
FIG. 24 illustrates positioning of a fixture about the needle shell and insertion of an insertion rod through the needle shell.

As shown by FIG. 24, fixture 330 is positioned about needle shell 22 and about implant tube 226. Fixture 330 is further positioned against skin 60. In one implementation, fixture 330 has an extendable side bar that extends partially along a length of needle shell 22 and includes an upper ring or C-shaped arm 333 which includes a clipper fastener for releasably clipping or attaching to insertion rod 28 and a lower donut or C-shaped arm 335 positioned against skin 60. In the example illustrated, arm 335 has a lower surface 338 configured to grip skin 60 to retain fixture 330 in place relative to skin 60. In one implementation, surface 338 comprises a tacky adhesive material which releasably adheres surface 338 to skin 60. In other implementations, surface 338 may include sharp points or other structures which grip skin 60.

Once the insertion rod 28 is held steady, the needle shell 22, along with implant tube 226 (shown in FIG. 22), are slid along rod 28 until withdrawn the length of an implant (or implants). This action leaves implant 29 in place below skin 60, where the implant 29 is retained by recoiled tissue. Thereafter, insertion rod 28, together with other components of the assembly may be removed. As noted above, in some implementations, implant tube 226 may be left in place, wherein implant tube 226 may serve as a catheter for supplying liquids to the location below skin 60.

Although the present disclosure has been described with reference to example embodiments, workers skilled in the art will recognize that changes may be made in form and detail without departing from the spirit and scope of the claimed subject matter. For example, although different example embodiments may have been described as including one or more features providing one or more benefits, it is contemplated that the described features may be interchanged with one another or alternatively be combined with one another in the described example embodiments or in other alternative embodiments. Because the technology of the present disclosure is relatively complex, not all changes in the technology are foreseeable. The present disclosure described with reference to the example embodiments and set forth in the following claims is manifestly intended to be as broad as possible. For example, unless specifically otherwise noted, the claims reciting a single particular element also encompass a plurality of such particular elements.

What is claimed is:

1. An apparatus comprising:
   a needle shell having an axial end adapted to be inserted below a surface of tissue that is to receive an implant and an opposite end opposite the axial end, the axial end having an axial opening;
   a removable implant tube slidable within the needle shell while the needle shell is adapted to be below the surface of the tissue that is to receive the implant, the removable implant tube having interior surfaces that are to contact and guide sliding movement of the implant that is to be contained within the removable implant tube; and
   an implant insertion rod within the removable implant tube, wherein the removable implant tube is capable of sliding within the needle shell relative to the needle shell while the needle shell is adapted to be retained below the surface of the tissue that is to receive the implant and wherein the removable implant tube is configured to be slidable within the needle shell to a depth below the surface of the tissue such that an entire length of the implant is configured to be movable through the axial opening so as to be located below the surface of the tissue that is to receive the implant while the implant is contained and circumferentially surrounded by both the needle shell and the removable implant tube, wherein the removable implant tube is configured to be slidable within the needle shell to a position below a surface of skin and wherein the removable implant tube extends from the axial end to the opposite end, the removable implant tube providing an imperforate lumen from the axial end to the opposite end through the axial opening of the needle shell at the opposite end and through which fluid may be directed.

2. The apparatus of claim 1 further comprising the implant within the removable implant tube, the implant having a first end facing a first end of the removable implant tube and a second end facing a second end of the removable implant tube, wherein the implant insertion rod has an axial end movable within the implant tube into abutment with the first end of the implant, the apparatus further comprising a fixture to be positioned directly against the surface of the skin and removably attached to the implant insertion rod and to allow movement of the implant tube and the needle shell simultaneously while the fixture is retained directly against the skin of an insertion site and is retaining the implant insertion rod with respect to the skin of the insertion site.

3. The apparatus of claim 2, wherein the fixture comprises a donut encircling the needle shell.

4. The apparatus of claim 1 further comprising the implant within the removable implant tube.

5. The apparatus of claim 1 further comprising a plurality of implants within the removable implant tube.

6. The apparatus of claim 1, wherein the axial end has a tapering pointed tip for penetrating tissue.

7. The apparatus of claim 1, wherein the removable implant tube and the needle shell are configured to be slidable relative to one another between a first position in which the removable implant tube is retracted within the needle shell and a second position in which the removable implant tube projects through the axial opening at the axial end of the needle shell beyond the axial end of the needle shell.

8. The apparatus of claim 1, wherein the needle shell has an interior in which the removable implant tube is received and wherein the removable implant tube is completely removable and withdrawable from the interior so as to be completely outside the interior and wherein the needle shell has an opening through which the completely withdrawn removable implant tube is insertable into the interior.

* * * * *